(12) United States Patent
Frieze et al.

(10) Patent No.: US 6,168,599 B1
(45) Date of Patent: Jan. 2, 2001

(54) LONG BONE REAMER

(76) Inventors: Allan S. Frieze, 45 Berkery Pl., Alpine, NJ (US) 07620-0472; David Nalepa, 429 W. 24$^{th}$ St. #B, New York, NY (US) 10011

( * ) Notice: Under 35 U.S.C. 154(b), the term of this patent shall be extended for 0 days.

(21) Appl. No.: 09/402,930

(22) PCT Filed: Apr. 14, 1997

(86) PCT No.: PCT/US97/06138

§ 371 Date: Oct. 13, 1999

§ 102(e) Date: Oct. 13, 1999

(87) PCT Pub. No.: WO98/46152

PCT Pub. Date: Oct. 22, 1998

(51) Int. Cl.$^7$ ............................................. A61B 17/56
(52) U.S. Cl. ............................ 606/80; 606/79; 408/227
(58) Field of Search ................. 606/80, 79, 82, 606/83, 84, 85, 86, 87, 89; 408/127, 204, 201, 207, 227

(56) References Cited

U.S. PATENT DOCUMENTS

| | | | | |
|---|---|---|---|---|
| 314,086 | * | 3/1885 | Waas | 408/127 |
| 3,554,192 | * | 1/1971 | Isberner | 606/80 |
| 3,633,583 | * | 1/1972 | Fishbein | 606/86 |
| 3,702,611 | * | 11/1972 | Fisbein | 606/80 |
| 4,473,070 | * | 9/1984 | Matthews et al. | 606/80 |
| 4,706,659 | * | 11/1987 | Matthews et al. | 606/80 |
| 5,100,267 | * | 3/1992 | Salyer | 606/81 |
| 5,116,165 | * | 5/1992 | Salyer | 606/81 |
| 5,122,134 | * | 6/1992 | Borzone et al. | 606/80 |
| 5,180,384 | * | 1/1993 | Mikhail | 606/80 |
| 5,190,548 | * | 3/1993 | Davis | 606/80 |
| 5,192,291 | * | 3/1993 | Pannek, Jr. | 606/159 |
| 5,211,645 | * | 5/1993 | Baumgart et al. | 606/86 |
| 5,222,959 | * | 6/1993 | Anis | 606/107 |
| 5,318,576 | * | 6/1994 | Plassche et al. | 606/159 |
| 5,376,092 | * | 12/1994 | Hein et al. | 606/81 |
| 5,464,406 | * | 11/1995 | Ritter et al. | 606/86 |
| 5,653,712 | * | 8/1997 | Stern | 606/80 |

* cited by examiner

*Primary Examiner*—Pedro Philogene
(74) *Attorney, Agent, or Firm*—Woodbridge & Associates, P.C.; Richard C. Woodbridge (57) ABSTRACT

A long bone reamer apparatus is assembled from a plurality of blades that interlink with each other. According to a first embodiment, six long cutting blades are held in position by a plurality of disks, each having six blade receiving slots spaced at 60 degrees with respect to each other. The longitudinal axis of each of the blade receiving slots is slightly offset from the center of the disk so that tabs on opposing blades contact and are welded to each other. According to a second embodiment of the invention, four blades are connected together in a boxlike arrangement having a long rod in the center thereof for support. A first set of the blades includes an interior aperture with a plurality of tabs which engage with a plurality of tab receiving slots in the second set of blades. Both sets of reamers have a head with blade portions arranged to lie along the surface of a semi-circle and, moreover, both embodiments have longitudinal sidewalls having cutting edges, which lie in the plane of a cylinder.

14 Claims, 7 Drawing Sheets

LONG BONE REAMER

BACKGROUND OF THE INVENTION

1. Field of the Invention

The invention relates to surgical long bone reamers formed from a plurality of interlocking blades.

2. Description of Related Art

The prior art patent literature discloses a small group of reamers and cutters for removing bone and tissue from joints that may be relevant to the state of the art. Many of those reamers are for shallow bone applications. For example, U.S. Pat. No. 4,621,637 entitled "SURGICAL DEVICE FOR REMOVING BONE AND TISSUE FROM JOINT MEMBERS" teaches a slotted, surgical device including a hemispheric housing that supports one or more cutting blades for bone and/or tissue cutting. Two and three blade embodiments are described. In both cases, the blades abut centrally of the device and interlock with the base at discrete points.

French Patent 1,031,888 describes a plurality of cutting blades which are radially disposed, equiangularly spaced atop a supporting plate and locked to the plate by fasteners. The resulting tool is used for cutting the acetabular portion of a hip prior to joint replacement.

Similarly, French Patent 1,041,311 describes a bone cavity forming tool which employs multiple blades in a hemispheric array.

Soviet Union Patent 1225-543-A entitled "BONE CUTTING TOOL FOR SURGERY" describes a cutter comprising multiple arcuate cutting elements extending from a central rod outwardly in an umbrella-like fashion.

French Patent 2,233,972 entitled "ARTIFICIAL HIP JOINT FITTING EQUIPMENT" describes another multi-blade, round headed milling cutter for acetabular applications.

U.S. Pat. No. 5,222,959 entitled "REMOVAL OF TISSUE" describes a soft tissue cutter having an oval, rather than hemispheric, shape.

U.S. Pat. No. 5,192,291 entitled "ROTATIONALLY EXPANDABLE ATHERECTOMY CUTTER ASSEMBLY" describes another soft tissue cutter in which the blades define a cylindrical, not hemispheric, structure.

U.S. Pat. No. 5,100,267 entitled "DISPOSABLE ACETABULAR REAMER CUP"describes a hemispheric, cup-shaped hip reamer. With regard to this structure, note also U.S. Pat. Nos. 5,116,165 and 5,376,092.

The following U.S. Patents describe prior art shallow bone reamers of possible interest, using multi-blade configurations, but for non-hip applications: U.S. Pat. Nos. 3,554,192; 5,122,134, 5,180,384 and 5,318,576.

In addition to shallow bone reamers, the prior art also discloses a few possibly relevant references to long bone reamers. For example, note U.S. Pat. No. 4,473,070 entitled INTRAMEDULLARY REAMER. That device includes a circular, replaceable blade that fits onto a grooved body member. There does not appear, however, to be any suggestion of interlinking or cross over blades.

U.S. Pat. No. 314,086 entitled BUNG CUTTER is of possible interest even though it does not relate to bone surgery. That references describes a structure including a mortised disk which rotates into position and includes a plurality of longitudinally extending cutters which seat in the disk via notches or mortises F on the periphery thereof. The structure, however, appears to relate primarily to cutting a bung hole in a barrel rather than reaming a hole therethrough.

The following patents are all cited as being of general interest only and are essentially the same in that they describe a reamer head for a long bone. The blades appear to generally radiate from a central portion and do not appear to be interlinked: U.S. Pat. Nos. 3,554,192; 4,706,659; 5,122,134; and, 5,190,548.

Lastly, U.S. Pat. No. 3,633,583 entitled ORTHOPEDIC SINGLE-BLADE BONE CUTTER and U.S. Pat. No. 5,211,645 entitled DEVICE FOR GUIDING AN INTERNAL SAW FOR LONG TUBULAR BONE OSTEOTOMY are cited as being as general relevance only.

While a few long and shallow joint reamers are known in the prior art, they tend to be expensive, or hard to construct, or both. There clearly appears to be a need for a safe, easy to assemble, inexpensive and effective reamer especially for the femur or tibia. Insofar as understood, none of the prior art known to the inventor, whether taken individually or in combination, hints, teaches or suggests the novel long bone reamer disclosed herein.

SUMMARY OF THE INVENTION

Briefly described, the invention comprises a long bone reamer including a plurality of interlinking cutting blades which, when assembled, has a cutting head or tip with a cutting edge which lies in a hemispherical plane.

According to a first embodiment of the invention, the reamer comprises six blades each having a straight, long side and a curved tip. The six blades are held in position by a plurality of disks each having six blade receiving slots therein. Each blade also includes an inside surface having a plurality of tabs which, when assembled on the disks, overlap each other. The six blades actually comprise three sets of two blades each wherein the tabs of each of the three sets are offset so that they don't interfere with each other. When properly assembled, each of the tabs of the three sets of blades overlap each other and may be welded in that position.

According to a second embodiment of the invention, four blades are assembled in a boxlike structure to form the long bone reamer. Two sets of blades include a hollow aperture with inwardly facing tabs thereon, which mate with corresponding slots in the second set of blades. A rod or similar structure is located in the hollow interior of the boxlike structure for additional support.

When properly assembled, each of the two embodiments has edges which when rotated, all lie in a semi-circular surface. Moreover, when each of the embodiments is rotated, the longitudinal cutting edges of each of the blades lie in a cylindrical plane. The resulting structure is safe, easy to assemble, inexpensive and effective as a long bone reamer.

The invention may be more fully understood by reference to the following drawings.

DETAILED DESCRIPTION OF THE INVENTION

During the course of this description, like numbers will be used to identify like elements according to the different figures that illustrate the invention.

Figure 1:
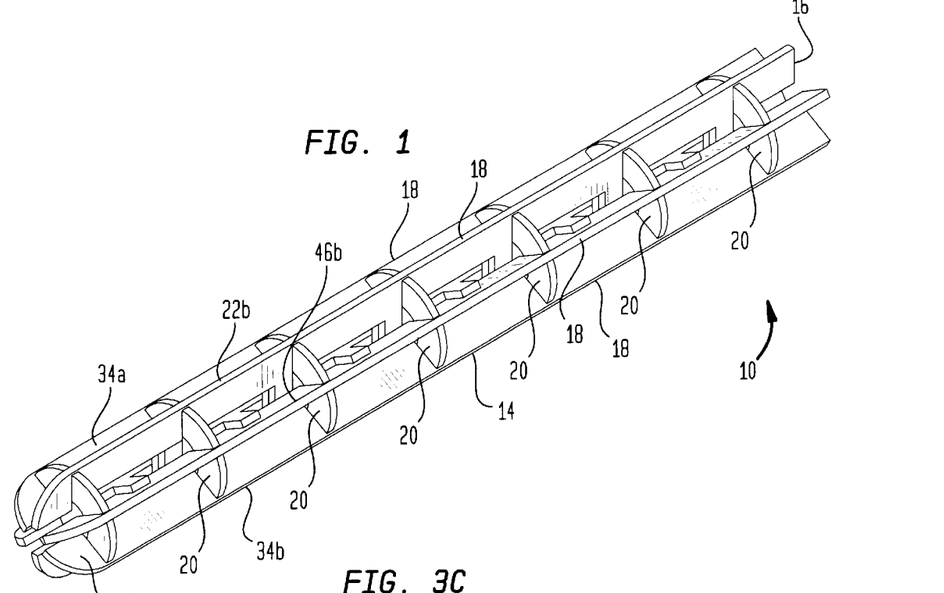
FIG. 1 is a perspective view of a large diameter, long bone reamer according to a first embodiment of the invention.
Figure 2:
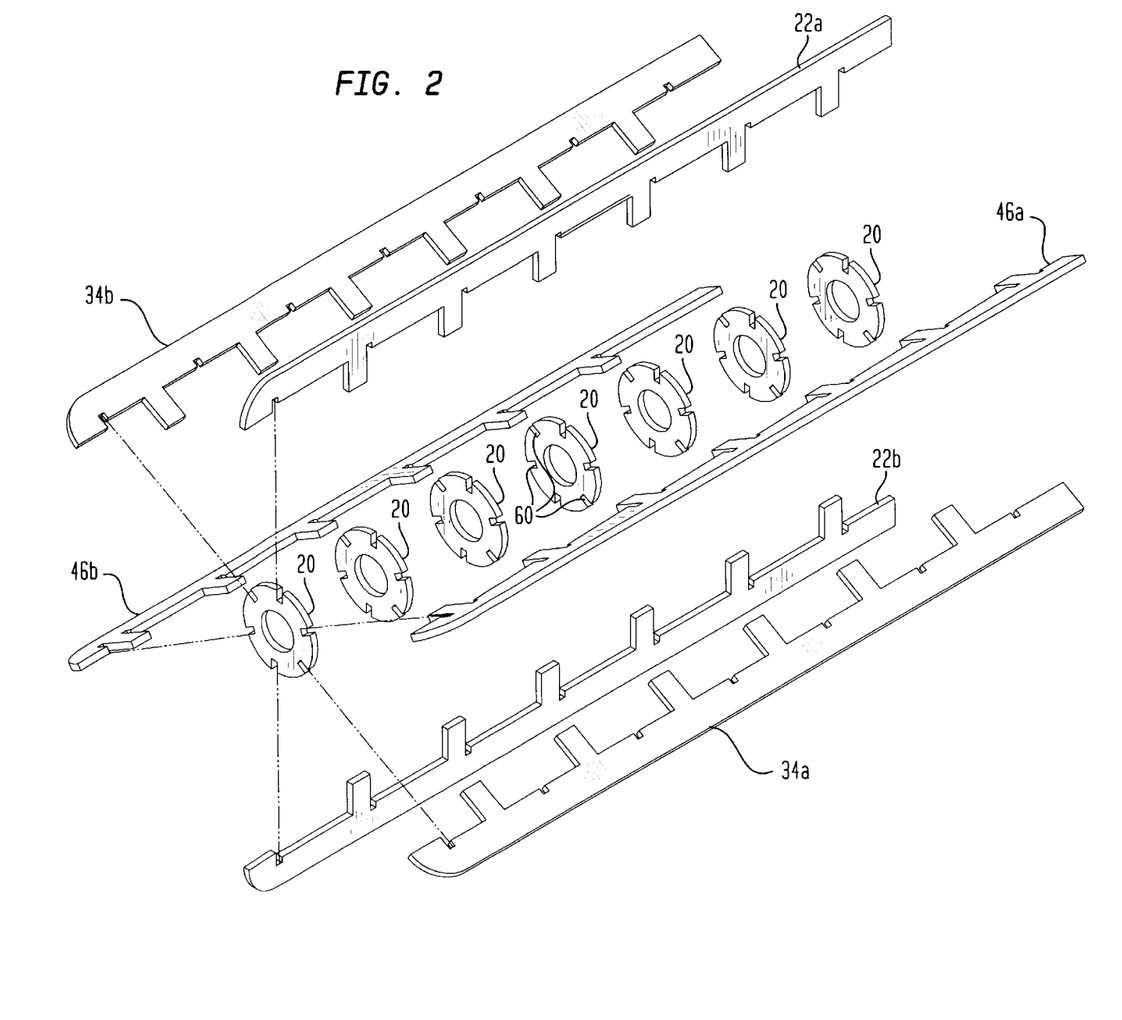
FIG. 2 is an exploded perspective view of the large diameter, long bone reamer of FIG. 1.

A large diameter long bone reamer 10 according a first embodiment of the invention is illustrated in FIG. 1. Each reamer 10 includes a rounded, hemispherical head 12, a plurality of blade edges 14 which lie in a cylindrical plane and a rear portion 16. Six long blades 18 are held in assembled position by disks 20. The six blades 18 are formed from three sets of two matching blades each. The first blade pair comprises blades 22a and 22b; the second blade pair comprises blades 34a and 34b and the third pair of blades comprises blades 46a and 46b. Details of the blades are shown in FIGS. 4A, 4B and 4C.

Figures 4A, 4B:
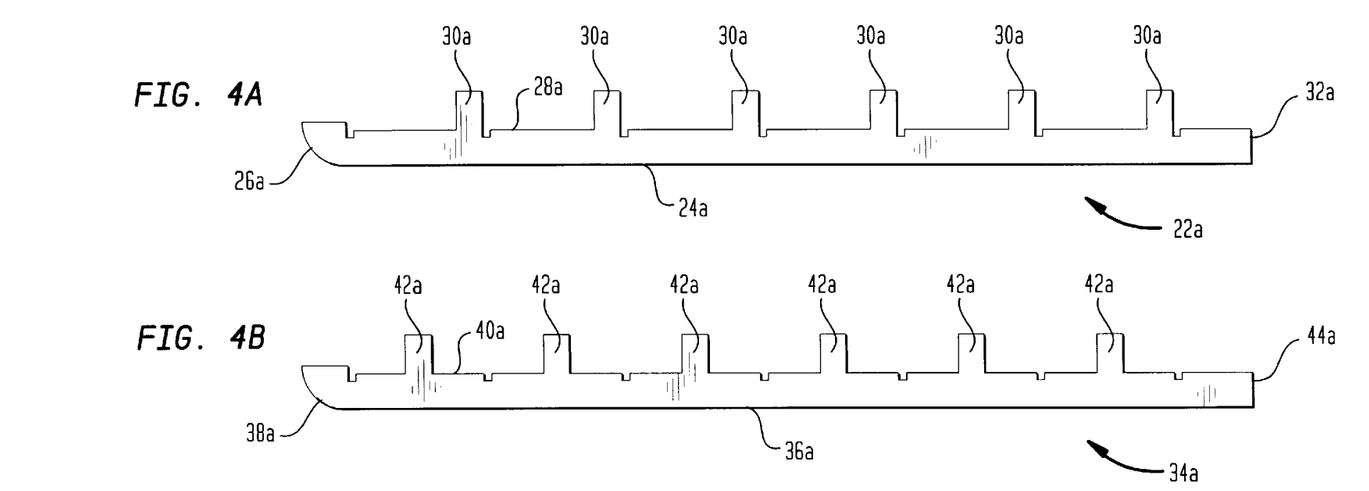
FIG. 4A illustrates one blade of the first set of blades of the large diameter, long bone reamer of FIG. 1.
FIG. 4B illustrates one blade of the second set of blades, of the large diameter, long bone reamer of FIG. 1.
Figure 4C:
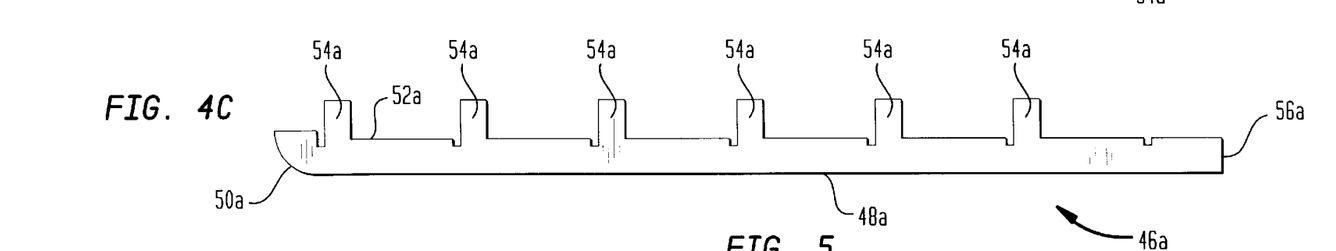
FIG. 4C illustrates one blade of the third set of blades of the large diameter, long bone reamer of FIG. 1.

FIG. 4A illustrates blade 22a of pair 22a and 22b. Blade 22b is substantially identical to 22a. Blades 22a and 22b each include a straight, longitudinal cutting edge 24a and 24b; a rounded cutting tip 26a and 26b, an inside edge 28a and 28b; tabs 30a and 30b located on the inside edges 28a and 28b; and a rear edge 32a and 32b. Likewise, blade 34a is illustrated in FIG. 4B but is substantially identical to its mating blade 34b. Blades 34a and 34b are similar, but not identical, to blades 22a, 22b, 46a and 46b. In particular, blades 34a and 34b each include a straight, longitudinal cutting edge 36a and 36b; a rounded cutting tip 38a and 38b;
an inside edge 40a and 40b; tabs 42a and 42b located on the inside edge 40a and 40b; and a rear edge 44a and 44b. Note that tabs 42a are offset with respect to the relative position of tabs 30a on blade 22a as shown in FIG. 4A. Lastly, blade 46a of blade pair 46a and 46b, is illustrated in FIG. 4C. Blade 46a is substantially identical to blade 46b. Both blades 46a and 46b each include a straight, longitudinal cutting edge 48a and 48b; a rounded cutting tip 50a and 50b; an inside edge 52a and 52b; tabs 54a and 54b located on the inside edges 52a and 52b, respectively; and, a rear end 56a and 56b. Tabs 54a and 54b are aligned to match with each other but are offset so that they do not align with tabs 42a and 42b of the first pair of blades 34a and 34b; nor do they align with tabs 30a and 30b of the first pair of blades 22a and 22b.

Figure 5:
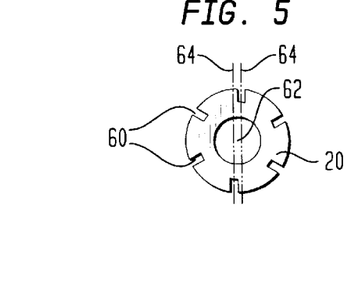
FIG. 5 is a front view of one of the supporting disks of the large diameter, long bone reamer of FIG. 1 showing the six blade receiving slots therein.

Blades 18 (22a, 22b, 34a, 34b, 46a and 46b) are received in slots 60 of the disks 20 illustrated in FIG. 5. Disks 20 have a center point 62 and each of the slots 60 has a major axis 64. Each axis 64 is slightly offset from disk center 62 so that tabs 30a, 30b, 42a, 42b, 54a and 54b overlap but do not interfere with each other.

Figure 3A:
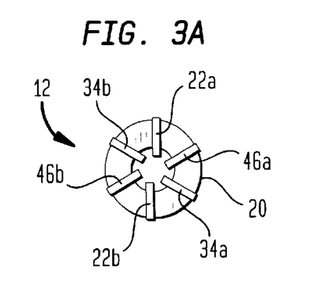
FIG. 3A is a front view of the large diameter, long bone reamer of FIG. 1.
Figure 3B:
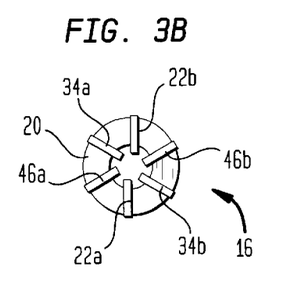
FIG. 3B is a rear view of the large diameter, long bone reamer of FIG. 1.
Figure 3C:
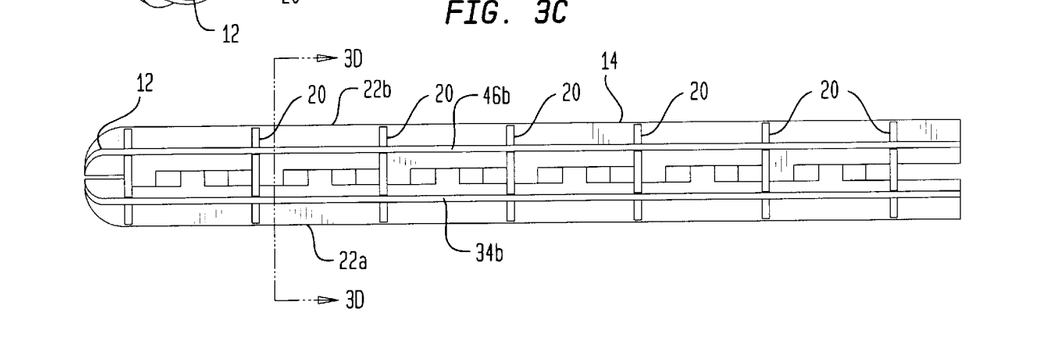
FIG. 3C is a side view of the large diameter, long bone reamer of FIG. 1.
Figure 3D:
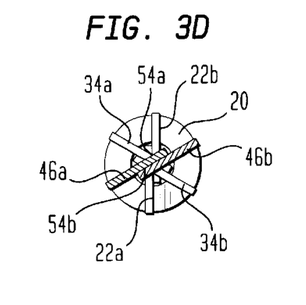
FIG. 3D is a cross sectional view of the large diameter, long bone reamer of FIG. 3C as seen from perspective 3D—3D.

When the apparatus 10 is assembled, the front tip 12 appears as shown in FIG. 3a and the rear end 16 appears as shown in FIG. 3B. FIG. 3D is a cross-sectional view of the assembled reamer 10 as illustrated in FIG. 3C and as seen from perspective 3D—3D. Note that tabs 54a and 54b of blades 46a and 46b overlap and touch each other. They are preferably welded in this position. In a similar fashion, tabs 30a and 30b of blades 22a and 22b overlap each other as do tabs 42a and 42b of blades 34a and 34b. To achieve this structure, slots 60 have a long access 64 that when extended slightly misses the center 62 of the disks 20 so that the tabs 30a, 30b, 42a, 42b and 54a and 54b slightly overlap each other and do not interfere. Tabs 30a, 42a, 54a are preferably welded respectively to tabs 30b, 42b and 54b.

When the apparatus 10 is assembled, the cutting tips 26a, 26b, 38a, 38b and 50a and 50b have edges which lie in essentially the same rounded, hemispherical plane so that the reamer 10 is rotated it cuts smoothly and evenly into the bone. Likewise, the sidewall 14 comprises the exterior long, straight cutting edges 24a, 24b, 36a, 36b, 48a and 48b all of which lie in the same, round cylindrical plane so that the reamer 10 is rotated, it cuts smoothly. The tabs may be welded to each other and/or disks 20 in order to keep the device in a permanent, assembled state.

The foregoing reamer is especially useful for large diameter, long bones. The interlinking of the blades gives the structure additional rigidity. In addition, it is relatively easy to manufacture and assemble and, therefore, it is inexpensive to distribute to the public.

Figure 6:
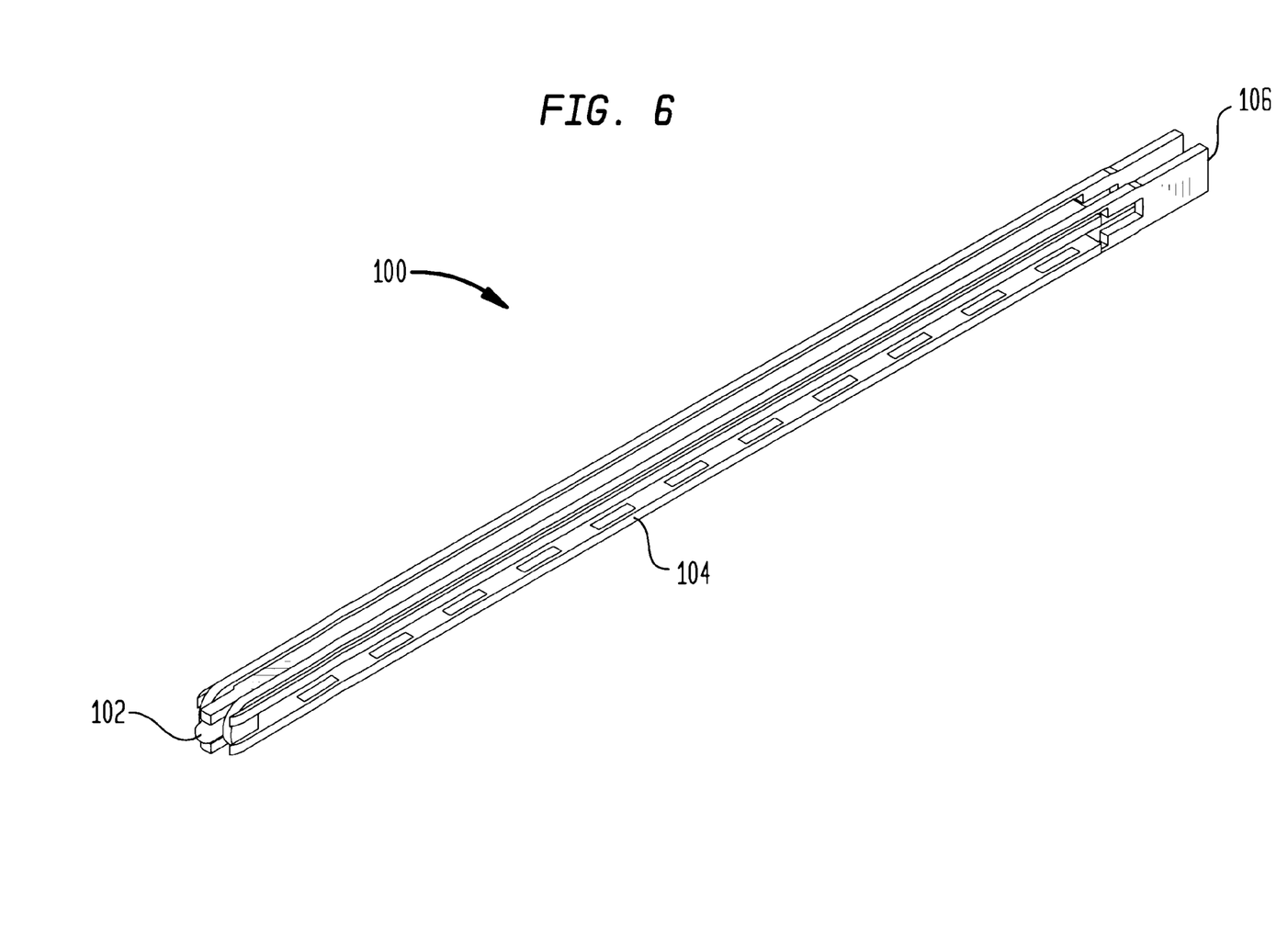
FIG. 6 is a perspective view of a small diameter, long bone reamer according to the preferred second embodiment of the invention.

FIG. 6 illustrates the second or preferred embodiment 100 of a small diameter, long bone reamer. The small diameter, long bone reamer 100 includes a cutting head 102, a cutting sidewall 104 and a rear end 106.

Figure 7:
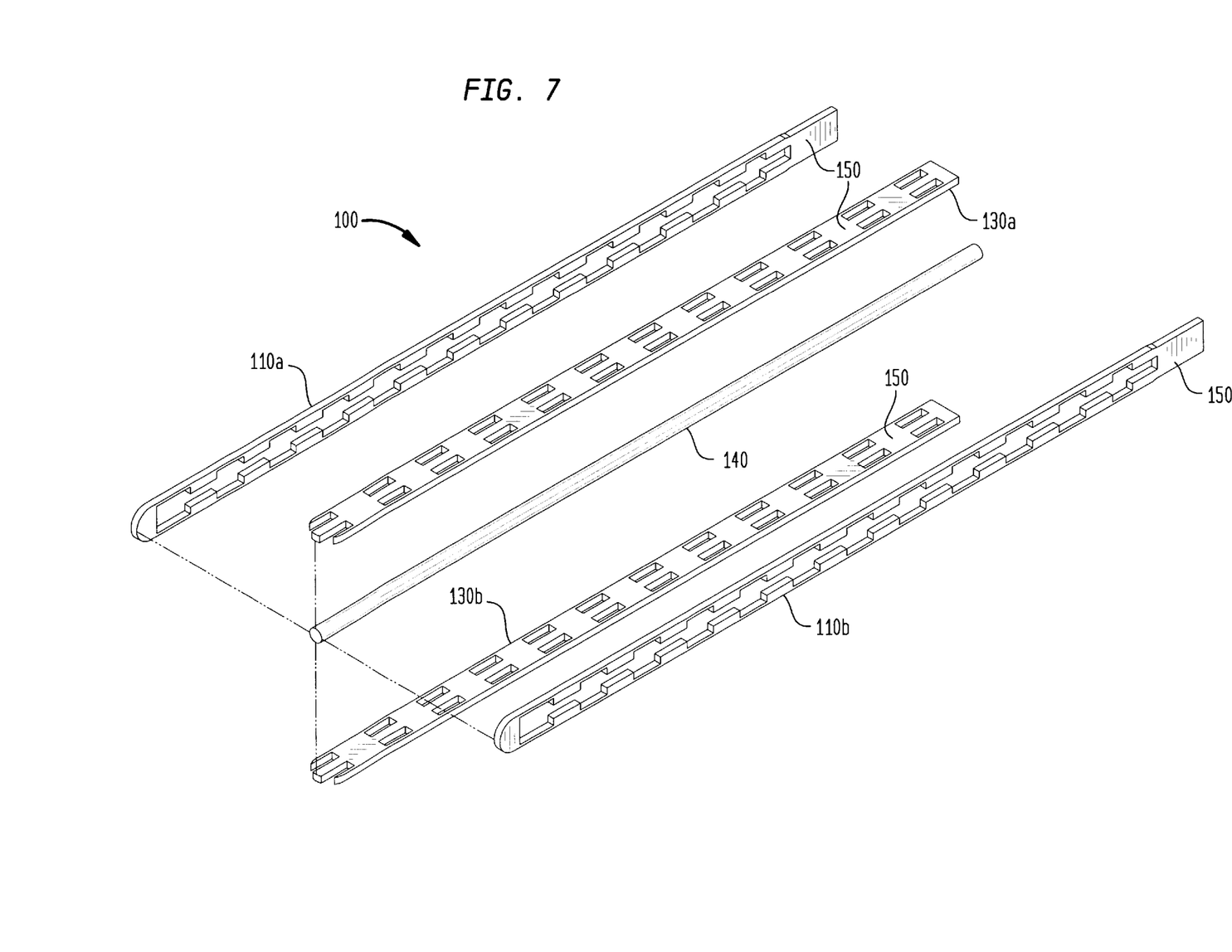
FIG. 7 is an exploded view of the small diameter, long bone reamer of FIG. 6.

FIG. 7 illustrates the small diameter, long bone reamer 100 in an exploded view. Reamer 100 includes a group of four blades 150 divided into two sets or pairs. The first pair of blades in the group 150 comprise elements 110a and 110b; the second pair of blades in the group 150 comprise elements 130a and 130b. A central rod 140 is received in the boxlike cavity formed by the blades and serves to give additional rigidity to the resulting structure.

Figure 9A:
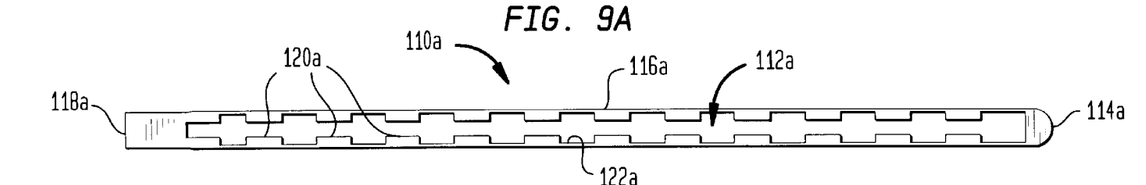
FIG. 9A is a top plan view of one of the two blades of the first set of blades included in the small diameter, long bone reamer of FIG. 6.

Blade 110a is illustrated in detail in FIG. 9A. Blade 110a is substantially identical to blade 110b and lies on the opposite side of the apparatus 10 from blade 110a. Blade 110a includes an interior cavity 112a, a rounded cutting tip 114a, a straight, longitudinal cutting edge 116a, a rear end 118a, and a plurality of inward facing tabs 120a along the two long edges 122a of the interior cavity 112a.

Figure 9B:
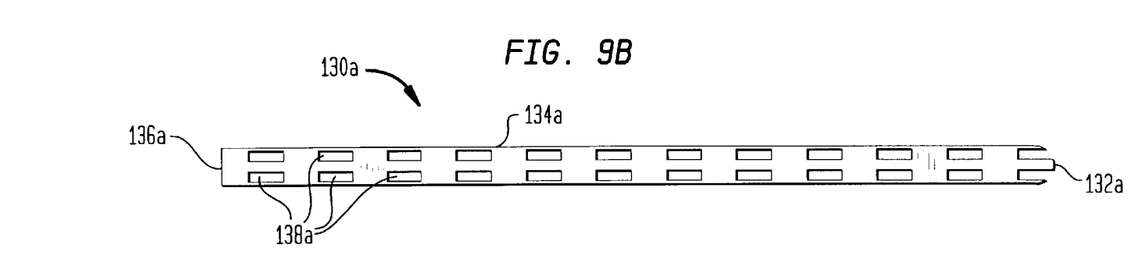
FIG. 9B is a top plan view of one of the two blades of the second set of blades included in the small diameter, long bone reamer of FIG. 6.

FIG. 9B illustrates blade 130a in detail. Blade 130a is substantially identical to blade 130b and includes a partially rounded cutting tip 132a, a long, straight, cutting edge 134a, a rear end 136a, and a plurality of tab receiving slots 138a. Slots 138a receive the tabs 120a and 120b of blades 110a and 110b of the first set.

Figure 8A:
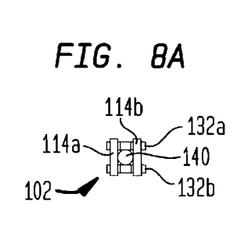
FIG. 8A is a front view of the small diameter, long bone reamer of FIG. 6.
Figure 8B:
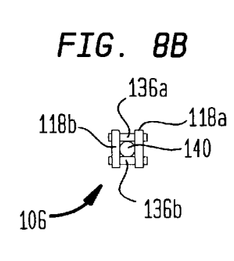
FIG. 8B is a rear view of the small diameter, long bone reamer of FIG. 6
Figure 8C:
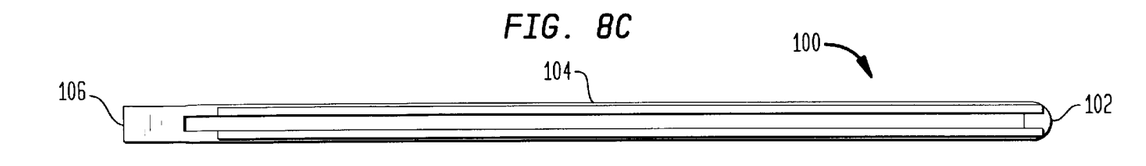
FIG. 8C is a side elevational view of the small diameter, long bone reamer of FIG. 6.
Figure 10:
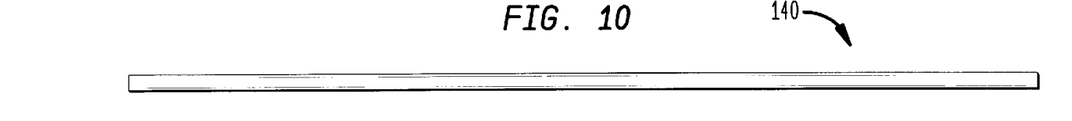
FIG. 10 illustrates the supporting and locking rod having a round cross section which goes down the center of the small diameter, long bone reamer.

The small diameter, long bone reamer 100, as seen in profile in FIG. 8C, is assembled in the following manner. First, the two blades 110a and 110b are placed side by side. Second, blade 130a is placed between the two blades 110a and 110b in such a way that tabs 120a and 120b engage the tab receiving slots 138a. Third, blade 130b is placed between blades 110a and 110b and has its slots 138a engaged with the remaining tabs 120a. Fourth, rod 140 is placed down the middle of the structure to keep the blades 130a and 130b in position with respect to the tabs on blades 110a and 110b. When properly assembled, the cutting head 102 appears as shown in FIG. 8A and the rear 106 of the device appears as shown in FIG. 8B. The central rod 140 is illustrated in FIG. 10.

When the small diameter, long bone reamer 100 is assembled as shown in FIGS. 6, 7 and 8C, the tips 114a, 114b, 132a and 132b have points which define a rounded, semi-circular form such that when the reamer 100 is rotated it cuts evenly and smoothly. Similarly, the cutting edges 116a, 116b, 134a and 134b define eight cutting edges which lie in a generally cylindrical plane such that when the reamer 100 is rotated it cuts smoothly.

The small diameter, long bone reamer 100 is somewhat different in structure from the large diameter, long bone reamer 10 because the dynamics of the cutting operation in a small bone are different from the dynamics of the cutting operation in a long bone. Four cutting blades 10a, 110b, 130a and 130b are required for the small diameter, long bone reamer because there isn't room to fit additional blades. In contrast, the large diameter, long bone reamer 10 has more room and, therefore, can accommodate six blades 18, namely blades 22a, 22b, 34a, 34b, 46a and 46b.

The small diameter, long bone reamer 100 according to the preferred embodiment of the invention is very strong, especially given the central support of rod 140; is relatively easy to manufacture; and, relatively inexpensive to distribute.

Figure 11:
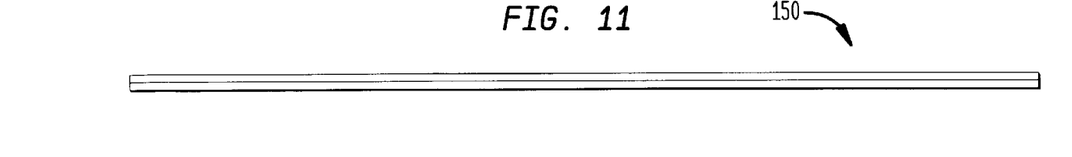
FIG. 11 illustrates an alternative supporting and locking rod having a square cross section.

Long bone reamer 100 can be modified to achieve different performance characteristics. First of all, the round rod 140 shown in FIG. 10 can also have a square cross section as shown by rod 150 in FIG. 11. A square rod 150 produces a more rigid reamer 100 and also helps to keep debris out of the middle channel of the apparatus. It has also been found that if the square rod is welded at just one location to the blade package that the reamer apparatus 100 becomes relatively flexible—a characteristic that is desirable if a femur or tibia is curved. It is also possible to replace the metal rod 140 or 150 with a high temperature plastic rod for additional flexibility and ease of cleaning.

The four blade second embodiment 100 is preferred over the six blade first embodiment 10 because it is easier to construct the four blade embodiment 100 in smaller diameter sizes. While the small diameter reamer 100 preferably has four blades it would be possible to use the same interlocking concept to construct a reamer 100 with 4, 6, 8, 10 blades, etc.

Figure 12:
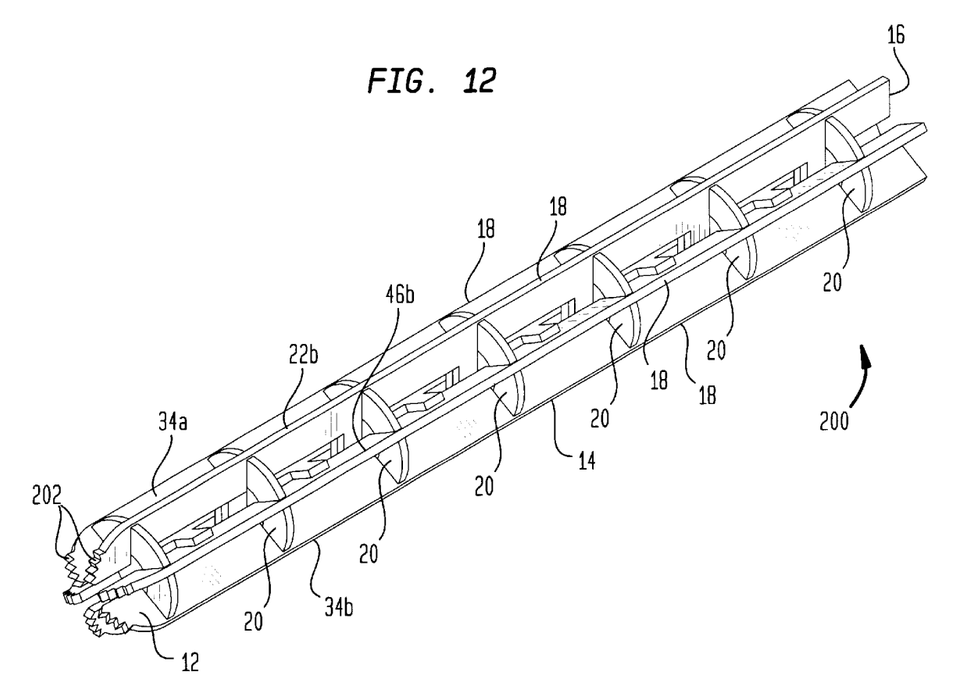
FIG. 12 illustrates a cylindrical reamer having cutting teeth on the leading edge thereof.

Lastly, it may be desirable to add teeth to the leading edge of reamer 10 (or reamer 100) so that the reamer 10 can both drill and ream. FIG. 12 illustrates such a reamer 200 having teeth 202 on its leading edge 12.

While the invention has been described with respect to the preferred embodiment thereof, it will be appreciated by those of ordinary skill in the art that various modifications can be made to the structure and function of the invention without departing from the spirit and scope thereof.

We claim:

1. A long bone reamer apparatus (10, 200) comprising:
   a plurality of N long blades (18), each blade, (22a, 22b, 34a, 34b, 46a, 46b) having a long, relatively straight cutting edge (24a, 24b, 36a, 36b, 48a, 48b) and a partially rounded leading cutting tip (26a, 26b, 38a, 38b, 50a, 50b); and,
   holding means (20) for holding said blades (22a, 22b, 34a, 34b, 46a, 46b) together, said holding means comprising a plurality of disks (20) each having a plurality of blade receiving slots (60) therein,
   wherein said reamer apparatus (10, 200) when assembled has a head portion (12) with cutting tips (26a, 26b, 38a, 38b, 50a, 50b) that lie in a semi-circular plane, and a side portion (14) with said cutting edges (24a, 24b, 36a, 36b, 48a, 48b) that lie in a cylindrical plane.

2. The apparatus of claim 1 wherein N equals at least three.

3. The apparatus of claim 2 wherein N equals at least four.

4. The apparatus of claim 3 wherein each blade (22a, 22b, 34a, 34b, 46a, 46b) has a plurality of tabs (30a, 30b, 42a, 42b, 54a, 54b) on side of said blade (28a, 28b, 40a, 40b, 52a, 52b) opposite from said side long, relatively straight cutting edge (24a, 24b, 36a, 36b, 48a, 48b),
   wherein said tabs (30a, 30b, 42a, 42b, 54a, 54b) of opposing blades contact and support each other.

5. The apparatus of claim 4 wherein N equals 6 and said blade receiving slots (60) in said disk are spaced approximately 60° with respect to each other.

6. The apparatus of claim 5 wherein said blade receiving slots (60) have a long axis (64) that bypasses the center (62) of said disks (20) so that said tabs (30a, 30b, 42a, 42b, 54a, 54b) can overlap without interfering with each other.

7. The apparatus (200) of claim 1 wherein said partially rounded cutting tips include teeth (202) thereon.

8. A long bone reamer apparatus (100) comprising:
   a plurality of N long blades (150), where N equals at least four, each blade (110a, 110b, 130a, 130b) having a long, relatively straight cutting edge (116a, 116b, 134a, 134b) and a partially rounded leading cutting tip (114a, 114b, 132a, 132b), said plurality of N long blades including a first set of blades (110a, 110b) each including an aperture (112a, 112b) therein, a pair of long opposing internal sides (122a, 122b), each internal side (122a, 122b) including a plurality of tabs (120a, 120b) thereon, and, a second set of blades (130a, 130b) having a plurality of tab receiving slots (138a, 138b) therein, wherein said first (110a, 110b) and second (130a, 130b) set of blades have cutting edges (116a, 116b, 134a, 134b) on the sides thereof; and,
   holding means (120a, 120b, 138a, 138b, 140) for holding said blades (110a, 110b, 130a, 130b) together,
   wherein said reamer apparatus (100) when assembled has a head portion (102) with cutting tips (102a, 102b, 132a, 132b) that lie in a semi-circular plane, and a side portion (104) with said cutting edges (116a, 116b, 134a, 134b) that lie in a cylindrical plane.

9. The apparatus of claim 8 further including a rod (140) means locatable on the inside of said reamer apparatus (100) for keeping said blades (110a, 110b, 130a, 130b) in an assembled condition.

10. The apparatus of claim 9 wherein said rod (140) has a round cross section.

11. The apparatus of claim 9 wherein said rod (150) has a square cross section.

12. The apparatus of claim 9 wherein said rod (140, 150) is formed by high temperature resistant plastic.

13. The apparatus of claim 9 wherein said rod (140, 150) is welded in at least one location to at least one of said blades (110a, 110b, 130a, 130b).

14. The apparatus (100) of claim 9 wherein said partially rounded cutting tips include teeth thereon.

\* \* \* \* \*